United States Patent
Tomikawa et al.

(10) Patent No.: US 11,596,602 B2
(45) Date of Patent: Mar. 7, 2023

(54) BIOCOMPATIBLE MATERIAL

(71) Applicant: FUJIFILM Corporation, Tokyo (JP)

(72) Inventors: Haruki Tomikawa, Ashigara-kami-gun (JP); Koji Takaku, Ashigara-kami-gun (JP); Kosuke Chiba, Ashigara-kami-gun (JP); Takafumi Hosokawa, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 237 days.

(21) Appl. No.: 17/186,229

(22) Filed: Feb. 26, 2021

(65) Prior Publication Data

US 2021/0177736 A1 Jun. 17, 2021

Related U.S. Application Data

(63) Continuation of application No. PCT/JP2019/032179, filed on Aug. 16, 2019.

(30) Foreign Application Priority Data

Aug. 30, 2018 (JP) .............................. JP2018-161928
May 13, 2019 (JP) .............................. JP2019-090566

(51) Int. Cl.
| | | |
|---|---|---|
| A61K 9/00 | (2006.01) | |
| A61K 9/51 | (2006.01) | |
| A61K 47/24 | (2006.01) | |
| A61K 47/26 | (2006.01) | |
| A61K 47/32 | (2006.01) | |

(52) U.S. Cl.
CPC ............ *A61K 9/006* (2013.01); *A61K 9/5161* (2013.01); *A61K 47/24* (2013.01); *A61K 47/26* (2013.01); *A61K 47/32* (2013.01)

(58) Field of Classification Search
None
See application file for complete search history.

(56) References Cited

U.S. PATENT DOCUMENTS

| | | |
|---|---|---|
| 5,144,016 A | 9/1992 | Skjak-Braek et al. |
| 5,147,648 A | 9/1992 | Bannert |

FOREIGN PATENT DOCUMENTS

| | | | |
|---|---|---|---|
| CN | 1329022 C | 8/2007 | |
| JP | 61-186307 A | 8/1986 | |
| JP | 63-502186 A | 8/1988 | |
| JP | 5-105701 A | 4/1993 | |
| JP | 2002-332248 A | 11/2002 | |
| JP | 2012-144490 A | 8/2012 | |
| JP | 2016-11293 A | 1/2016 | |
| JP | 2017-19794 A | 1/2017 | |
| WO | WO 2007/125533 A2 | 11/2007 | |
| WO | WO-2011125798 A1 * | 10/2011 | ........... A61K 31/522 |

OTHER PUBLICATIONS

Lee et al. (Alginate: properties and biomedical applications, Jan. 2012). (Year: 2012).*
Extended European Search Report for European Application No. 19856064.1, dated Sep. 28, 2021.
Japanese Office Action for corresponding Japanese Application No. 2020-539358, dated Dec. 14, 2021, with English translation.
International Preliminary Report on Patentability and Written Opinion of the International Searching Authority (Forms PCT/IB/326, PCT/IB/373, and PCT/ISA/237) for International Application No. PCT/JP2019/032179, dated Mar. 11, 2021, with English translation of the Written Opinion.
International Search Report (Form PCT/ISA/210) for International Application No. PCT/JP2019/032179, dated Oct. 1, 2019, with English translation.
Yang et al., "Strengthening Alginate/Polyacrylamide Hydrogenesis Using Various Multivalent Cations," ACS Applied Materials & Interfaces, vol. 5, Oct. 15, 2013, pp. 10418-10422.

* cited by examiner

*Primary Examiner* — Melissa S Mercier
(74) *Attorney, Agent, or Firm* — Birch, Stewart, Kolasch & Birch, LLP

(57) ABSTRACT

Provided is a biocompatible material capable of forming a gel having excellent retention and scratch resistance. The biocompatible material according to the embodiment of the present invention includes an alginate having a weight-average molecular weight of 1 million or more, an aluminum compound, a carboxyvinyl polymer, and an oil-based base material. However, the biocompatible material is substantially free of water.

22 Claims, No Drawings

BIOCOMPATIBLE MATERIAL

CROSS-REFERENCE TO RELATED APPLICATIONS

This application is a Continuation of PCT International Application No. PCT/JP2019/032179 filed on Aug. 16, 2019, which claims priority under 35 U.S.C. § 119(a) to Japanese Patent Application No. 2018-161928 filed on Aug. 30, 2018 and Japanese Patent Application No. 2019-090566 filed on May 13, 2019. Each of the above applications is hereby expressly incorporated by reference, in its entirety, into the present application.

BACKGROUND OF THE INVENTION

1. Field of the Invention

The present invention relates to a biocompatible material.

2. Description of the Related Art

In cancer patients, cancer treatment affects the mucous membrane of the mouth and, stomatitis occurs easily. For example, in anti-cancer drug treatment, in radiation therapy for head and neck cancer (cancer in the range from the head to the neck) in a case where a drug that easily causes stomatitis is administered, when radiation is directly applied to the mucous membrane of the mouth, stomatitis is inevitable. The pain of stomatitis is so strong that it is difficult to eat a meal by mouth.

As a symptomatic treatment for stomatitis, a patch (for example, Aphthaseal® 25 μg, manufactured by Taisho Pharma Co., Ltd., active ingredient: triamcinolone acetonide) that is directly attached to the affected part, an ointment (for example, Dexaltin oral ointment for oral cavity, manufactured by Nippon Kayaku Co., Ltd., active ingredient: dexamethasone) that is applied to the affected part, and a spray agent (for example, Salcoat® capsule for oral spray 50 μg, TEIJIN PHARMA LIMITED, active ingredient: beclomethasone propionate ester) that is sprayed on the affected part are mentioned.

However, these therapeutic agents contain steroids which are immunosuppressive agents, as active ingredients, and thus are not desirable for cancer patients.

In addition, when eating a meal by mouth, the patch attached to the affected part may be peeled off, or the ointment or the spray agent applied to the affected part may be lost, and thus the pain of stomatitis cannot be suppressed.

Accordingly, a biocompatible material capable of suppressing such pain of stomatitis has been desired.

For example, JP2012-144490A discloses "a composition for external use containing one or more selected from the group consisting of a mono-fatty acid polyethylene glycol and a compound having a fatty acid having 18 carbon atoms in a molecule among a trifatty acid polyoxyethylene sorbitans and one or more selected from the group consisting of glycyrrhetinic acid and a derivative thereof" (claim 1).

In addition, JP2016-011293A discloses "an oral cavity attachment film preparation containing at least one selected from a carboxyvinyl polymer and gum tragacanth, xanthan gum, gellan gum, carrageenan, or sodium alginate" (claim 1).

SUMMARY OF THE INVENTION

However, in a case of applying the composition for external use disclosed in JP2012-144490A to the oral cavity mucous membrane and being moistened, scratch resistance (residuality on the mucous membrane when friction is applied) and retention (attachability to the mucous membrane in a moist environment) were not sufficient.

In addition, in a case of applying the oral cavity attachment film preparation disclosed in JP2016-011293A to the oral cavity mucous membrane and being moistened, scratch resistance (residuality on the mucous membrane when friction is applied) reached the comparable level, but followability to mucous membrane expansion and contraction was low and retention (attachability to the mucous membrane in a moist environment) was not sufficient.

An object of the present invention is to provide a biocompatible material capable of forming a gel having excellent retention and scratch resistance.

As a result of diligent studies to solve the above-described problems, the inventors of the present invention have completed the present invention having the following configurations.

(1) A biocompatible material comprising, an alginate having a weight-average molecular weight of 1 million or more, an aluminum compound, a carboxyvinyl polymer, and an oil-based base material, in which the biocompatible material is substantially free of water.

(2) The biocompatible material according to (1), further comprising at least one selected from the group consisting of a sugar alcohol and a sugar.

(3) The biocompatible material according to (2), in which the at least one selected from the group consisting of a sugar alcohol and a sugar is at least one selected from the group consisting of erythritol, xylitol, mannitol, sorbitol, glucose, galactose, sucrose, trehalose, and lactose.

(4) The biocompatible material according to any one of (1) to (3), in which the alginate is at least one selected from the group consisting of sodium alginate, potassium alginate, and ammonium alginate.

(5) The biocompatible material according to any one of (1) to (4), in which the alginate has a weight-average molecular weight of 2 million or more.

(6) The biocompatible material according to any one of (1) to (5), in which the alginate has a weight-average molecular weight of 3 million or more.

(7) The biocompatible material according to any one of (1) to (6), in which the alginate has a weight-average molecular weight of 4 million or more.

(8) The biocompatible material according to any one of (1) to (7), in which the alginate is in a form of a particle, and an average particle size of the particles of the alginate is 50 μm or more and less than 300 μm.

(9) The biocompatible material according to (8), in which the average particle size of the alginate is 110 μm or more and less than 200 μm.

(10) The biocompatible material according to any one of (1) to (9), in which the aluminum compound is aluminum lactate.

(11) The biocompatible material according to any one of (1) to (10), in which a content of the aluminum compound is 0.1% by mass to 5.0% by mass with respect to a total mass of the biocompatible material.

(12) The biocompatible material according to any one of (1) to (11), in which a content of the aluminum compound is 1.0% by mass to 4.5% by mass with respect to a total mass of the biocompatible material.

(13) The biocompatible material according to any one of (1) to (12), in which an aqueous solution of the carboxyvinyl polymer having a concentration of 0.5% by mass has a viscosity of 20,000 cP or less at pH 7.5.

(14) The biocompatible material according to any one of (1) to (13), in which a content of the alginate is 5.0% by mass to 35.0% by mass with respect to a total mass of the biocompatible material.

(15) The biocompatible material according to any one of (1) to (14), in which a content of the alginate is 10.0% by mass to 30.0% by mass with respect to a total mass of the biocompatible material.

(16) The biocompatible material according to any one of (1) to (15), in which a value of a ratio of a content of the alginate to a content of the carboxyvinyl polymer is 0.5 to 5.5.

(17) The biocompatible material according to any one of (1) to (16), in which a value of a ratio of a content of the alginate to a content of the carboxyvinyl polymer is 1.0 to 5.5.

(18) The biocompatible material according to any one of (1) to (17), in which the oil-based base material contains a gelated hydrocarbon.

(19) The biocompatible material according to any one of (1) to (18), in which a value of a ratio of a content of the alginate to a content of the oil-based base material is 0.20 to 0.50.

(20) The biocompatible material according to any one of (1) to (19), in which the biocompatible material is for living body protection.

(21) The biocompatible material according to any one of (1) to (20), in which the biocompatible material is a mucous membrane protective agent.

(22) The biocompatible material according to (21), in which the biocompatible material is an oral cavity mucous membrane protective agent.

According to the present invention, a biocompatible material capable of forming a gel having excellent retention and scratch resistance can be provided.

DESCRIPTION OF THE PREFERRED EMBODIMENTS

In the present specification, the range indicated by using "to" means a range including both ends before and after "to". For example, a range indicated by "A to B" includes A and B.

[Biocompatible Material]

A biocompatible material according to the embodiment of the present invention includes an alginate having a weight-average molecular weight of 1 million or more, an aluminum compound, a carboxyvinyl polymer, and an oil-based base material. However, the biocompatible material is substantially free of water.

In the present specification, the biocompatible material means a material that attaches well to a biological surface (for example, skin, mucous membrane (for example, the mucous membrane in the oral cavity), eyes, teeth, tongue, nails, and hair). Further, as will be described later, since the biocompatible material according to the embodiment of the present invention absorbs water to form a crosslinked structure, a gel that is formed from the biocompatible material according to the embodiment of the present invention more strongly attaches to the biological surface. The biocompatible material according to the embodiment of the present invention has no adverse effect on the living body and is well compatible with the living body.

The biological surface may be in a healthy state or may have a wound or an ulcer.

As will be described later, the biocompatible material according to the embodiment of the present invention can form a crosslinked structure in a case of coming into contact with water. As the water, water present on the biological surface (for example, the surface in the oral cavity) may be used, or water may be added for the purpose of promoting attachability. In a case where the biocompatible material according to the embodiment of the present invention comes into contact with water to form a gel having a crosslinked structure, the attachability of the formed gel to the biological surface is stronger than the attachability of the biocompatible material to the biological surface before forming the crosslinked structure.

Further, the gel that is gel formed from the biocompatible material according to the embodiment of the present invention preferably has a function of protecting the biological surface, to which the biocompatible material is attached, from external stimuli. In order to achieve this purpose, the gel that is gel formed from the biocompatible material according to the embodiment of the present invention preferably has a physical strength of at least a certain level. Further, the gel that is gel formed from the biocompatible material according to the embodiment of the present invention may have lubricity on the surface of the non-adhesive surface.

The living body includes humans and animals other than humans (for example, mammals). Examples of the animals other than humans include primates, rodents (mice, rats, and the like), rabbits, dogs, cats, pigs, cows, sheep, and horses.

<Alginate Having a Weight-Average Molecular Weight of 1 Million or More>

<<Weight-Average Molecular Weight of Alginate>>

The weight-average molecular weight of the alginate is not particularly limited as long as it is 1 million or more; however, it is preferably 2 million or more, more preferably 3 million or more, still more preferably 3.5 million or more, and even still more preferably 4 million. In a case where the weight-average molecular weight of the alginate is 4 million or more, the scratch resistance is more excellent.

If the weight-average molecular weight of the alginate is less than 1 million, the scratch resistance of the gel to be formed is not sufficient and the residuality on the mucous membrane is low.

The upper limit of the weight-average molecular weight of the alginate is not particularly limited; however, it is preferably 10 million or less, more preferably 5 million or less, and still more preferably 4.5 million or less.

The weight-average molecular weight of the alginate can be measured using gel permeation chromatography (GPC). The GPC measurement conditions for measuring the weight-average molecular weight of the alginate are described below.

GPC measurement conditions
Column: TSKgel G6000+G4000+G2500 PWXL
Eluent: 0.2 mol/L sodium nitrate
Flow rate: 0.7 mL/min
Injection volume: 50 μL
Sample concentration: 0.1%
Analysis time: 60 minutes
Detection: Refractive Index (RI)

<<Average Particle Size of Particles of Alginate>>

The alginate may be in the form of particles.

The average particle size of the particles of the alginate is not particularly limited; however it is preferably 50 μm or more and less than 300 μm, and more preferably 110 μm or more and less than 200 In a case where the average particle size of the alginate is 110 μm or more and less than 200 the scratch resistance is more excellent.

The average particle size of the particles of the alginate is an average diameter measured using a wet/dry particle size distribution measuring device (LS 13 320, manufactured by Beckman Coulter Inc.).

<<Kind of Alginate>>

The alginate is not particularly limited as long as it is a salt of alginic acid; however, it is preferably a monovalent metal salt or an ammonium salt of alginic acid, more preferably one selected from the group consisting of sodium alginate, potassium alginate, and ammonium alginate, and still more preferably sodium alginate.

Quantitative and qualitative analysis of a monovalent cation constituting the alginate can be performed by ion chromatography.

Measurement conditions

Column: ion exchange resin (inner diameter: 4.0 mm, length: 25 cm)

Mobile phase: methanesulfonic acid solution (20 mmol/L)

Flow rate: 1.0 mL/min

Sample injection volume: 25 μL

Column temperature: 40° C.

Suppressor: electrodialysis type

Detector: electrical conductivity detector (30° C.)

<<Content of Alginate>>

The content of the alginate in the biocompatible material according to the embodiment of the present invention is not particularly limited; however, it is preferably 5.0% by mass to 35.0% by mass and more preferably 10.0% by mass to 30.0% by mass, with respect to the total mass of the biocompatible material according to the embodiment of the present invention. In a case where the content of the alginate is 10.0% by mass to 30.0% by mass with respect to the total mass of the biocompatible material according to the embodiment of the present invention, scratch resistance is more excellent in a case where the biocompatible material is gelated.

<Aluminum Compound>

<<Kind of Aluminum Compound>>

The aluminum compound is not particularly limited as long as it is a compound containing aluminum; however, it is preferably a water-soluble aluminum compound, more preferably a carboxylate of aluminum, still more preferably a hydroxycarboxylate of aluminum, and even still more preferably aluminum lactate. In a case where the aluminum compound is aluminum lactate, the retention of the biocompatible material is excellent in a case where the biocompatible material is gelated.

Examples of the water-soluble aluminum compound include aluminum chloride ($AlCl_3$), aluminum sulfate ($Al_2(SO_4)_3$), aluminum nitrate ($Al(NO_3)_3$), an ammonium alum ($AlNH_4(SO_4)_2 \cdot 12H_2O$), a potassium alum ($AlK(SO_4)_2 \cdot 12H_2O$), aluminum acetate, aluminum propionate, aluminum glycolate (aluminum hydroxyacetate), aluminum lactate, aluminum malate, aluminum tartrate, aluminum citrate, and aluminum isocitrate but the examples are not limited to thereto.

Examples of the carboxylate of aluminum include aluminum acetate, aluminum propionate, aluminum glycolate (aluminum hydroxyacetate), aluminum lactate, aluminum malate, aluminum tartrate, aluminum citrate, and aluminum isocitrate but are not limited to thereto.

Examples of the hydroxycarboxylate of aluminum include aluminum glycolate (aluminum hydroxyacetate), aluminum lactate, aluminum malate, aluminum tartrate, aluminum citrate, and aluminum isocitrate but are not limited to thereto.

<<Content of Aluminum Compound>>

The content of the aluminum compound in the biocompatible material according to the embodiment of the present invention is not particularly limited; however, it is preferably 0.1% by mass to 5.0% by mass and more preferably 1.0% by mass to 4.5% by mass, with respect to the total mass of the biocompatible material according to the embodiment of the present invention. In a case where the content of the aluminum compound is 1.0% by mass to 4.5% by mass with respect to the total mass of the biocompatible material according to the embodiment of the present invention, retention is more excellent in a case where the biocompatible material is gelated.

<Carboxyvinyl Polymer>

The carboxyvinyl polymer is a water-soluble vinyl polymer having a carboxy group, and specifically is a polymer having a crosslinked structure with acrylic acid and/or methacrylic acid as the main chain. Examples of the crosslinked structure include a crosslinked structure using an allyl sucrose or an allyl ether of pentaerythritol.

The biocompatible material according to the embodiment of the present invention is gelated by being brought into contact with water and has excellent scratch resistance and retention due to the network of the alginate gel formed by crosslinking of the alginate by aluminum ions and the network of the carboxyvinyl polymer.

The viscosity of the carboxyvinyl polymer is not particularly limited; however, it is preferably 20,000 cP or less, and more preferably 2,000 cP to 20,000 cP in a 0.5% by mass of an aqueous solution (25° C.) adjusted to pH 7.5. In a case where the viscosity of the 0.5% by mass of an aqueous solution (25° C.) of the carboxyvinyl polymer at pH 7.5 is 20,000 cP or less, scratch resistance and retention are more excellent in a case where the biocompatible material is gelated.

The viscosity of the carboxyvinyl polymer is a value measured by using a rheometer (MCR301, manufactured by Anton Paar GmbH) with an aqueous solution of the carboxyvinyl polymer having a concentration of 0.5% by mass at a shear rate of 1 (1/s), GAP of 0.05 mm, and 25° C.

In the biocompatible material according to the embodiment of the present invention, a commercially available product can be used as the carboxyvinyl polymer. Specific examples of the commercially available carboxyvinyl polymer include "CARBOPOL 971", "CARBOPOL 974", "CARBOPOL 980", and "CARBOPOL 981", which are manufactured by Lubrizol Advanced Materials; "HIVISWAKO 103", "HIVISWAKO 104", and "HIVISWAKO 105", which are manufactured by FUJIFILM Wako Pure Chemical Corporation; "Junron PW-120", "Junron PW-121", and "Junron PW-312S", which are manufactured by TOAGOSEI CO., LTD.; "AQUAPEC HV-501E", "AQUAPEC HV-505E", and "AQUAPE CH-V805", which are manufactured by SUMITOMO SEIKA CHEMICALS CO., LTD.; and "Synthalen K" and "Synthalen L" manufactured by 3V Sigma S.p.A.

In the biocompatible material according to the embodiment of the present invention, one kind of the carboxyvinyl polymer may be used alone, or two or more kinds thereof may be used in combination.

<<Content Ratio of Alginate to Carboxyvinyl Polymer>>

In the biocompatible material according to the embodiment of the present invention, the value of the ratio (mass ratio) [content of alginate/content of carboxyvinyl polymer] of the content of the alginate to the content of the carboxyvinyl polymer is not particularly limited; however, it is preferably 0.5 to 5.5 and more preferably 1.0 to 5.5. In a case where the [content of alginate/content of carboxyvinyl polymer] is in the range of 0.5 to 5.5, the retention of the formed gel is more excellent, and in a case where the [content of alginate/content of carboxyvinyl polymer] is in the range of 1.0 to 5.5, scratch resistance is more excellent in addition to the retention.

<Oil-Based Base Material>

The biocompatible material according to the embodiment of the present invention includes an oil-based base material. In a case where the biocompatible material according to the embodiment of the present invention includes an oil-based base material, the spreadability and adhesivity of the biocompatible material is more excellent.

The oil-based base material means a component that does not mix with water.

The viscosity of the oil-based base material is not particularly limited; however, it is preferably 100 to 1,000,000 cP and more preferably 1000 to 100,000 cP since the adhesion is more excellent when the biocompatible material according to the embodiment of the present invention is gelated. The viscosity is measured using a viscoelasticity measuring device (MCR302) at a measurement temperature of 25° C. and a shear rate of 1 (1/s).

Examples of the oil-based base material include raw materials used for ordinary oil-based ointments, for example, hydrocarbons (preferably gelated hydrocarbons), waxes, vegetable oils, animal oils, neutral lipids, synthetic oils and fats, sterol derivatives, monoalcohol carboxylic acid esters, oxyacid esters, polyhydric alcohol fatty acid esters, silicones, higher alcohols, higher fatty acids, and fluorine-based oils.

The oil-based base material may be used alone or in a combination of two or more kinds.

In a case where two or more kinds of oil-based base materials are used, a combination of hydrocarbons (preferably gelated hydrocarbons) and liquid paraffin is preferable.

As the gelated hydrocarbon, one that conforms to the "gelated hydrocarbon" of the pharmaceutical additive standard can be used, and more specifically, a gelated hydrocarbon obtained by gelating liquid paraffin with polyethylene can be preferably used.

The gelated hydrocarbon is preferably Plastibase (manufactured by Taisho Pharma Co., Ltd.) or HICALL GEL (manufactured by KANEDA Co., Ltd.).

Examples of the hydrocarbons include liquid paraffin (mineral oil), heavy liquid isoparaffin, light liquid isoparaffin, an α-olefin oligomer, polyisobutene, hydrogenated polyisobutene, polybutene, squalane, olive-derived squalane, squalene, vaseline, and solid paraffin.

The vaseline is preferably selected from those suitable for "vaseline", "white vaseline" or "yellow vaseline", which conforms to the Japanese Pharmacopoeia or a standard equivalent thereto.

Examples of the waxes include candelilla wax, carnauba wax, rice wax, Japanese wax, beeswax, montan wax, ozokerite, ceresin, microcrystalline wax, petrolatum, Fischer-Tropsch wax, polyethylene wax, and ethylene-propylene copolymer.

Examples of the vegetable oil include soybean oil, sesame oil, olive oil, coconut oil, palm oil, rice oil, cottonseed oil, sunflower oil, rice bran oil, cacao butter, corn oil, safflower oil, and rapeseed oil.

Examples of the animal oil include mink oil, turtle oil, fish oil, cow oil, horse oil, lard, and shark squalane.

Examples of the neutral lipids include triolein, trilinolein, trimyristin, tristearin, and triarachidonin.

Examples of the synthetic oils and fats include phospholipids and azone.

Examples of the sterol derivatives include dihydrocholesterol, lanosterol, dihydrolanosterol, phytosterols, cholic acid, and cholesteryl linoleate.

Examples of the monoalcohol carboxylic acid esters include octyldodecyl myristate, hexyldecyl myristate, octyldodecyl isostearate, and cetyl parimitinate.

Examples of the oxyacid esters include cetyl lactate, diisostearyl malate, and hydrogenated monoisostearic acid castor oil.

Examples of the polyhydric alcohol fatty acid esters include glyceryl trioctanoate, glyceryl trioleate, glyceryl triisostearate, glyceryl diisostearate, and tri(caprylic acid/capric acid)glycerycine.

Examples of the silicones include dimethicone (dimethylpolysiloxane), highly polymerized dimethicone (highly polymerized dimethylpolysiloxane), cyclomethicone (cyclic dimethylsiloxane, decamethylcyclopentasiloxane), and phenyltrimethicone.

Examples of the higher alcohols include cetanol, myristyl alcohol, oleyl alcohol, lauryl alcohol, cetostearyl alcohol, and stearyl alcohol.

Examples of the higher fatty acids include lauric acid, myristic acid, palmitic acid, stearic acid, isostearic acid, behenic acid, undecylene acid, 12-hydroxystearic acid, and palmitoleic acid.

Examples of the fluorine-based oils include perfluorodecane, perfluorooctane, and perfluoropolyether.

The content of the oil-based base material in the biocompatible material according to the embodiment of the present invention is not particularly limited; however, it is preferably 40% by mass to 80% by mass and more preferably 50% by mass to 70% by mass, with respect to the total mass of the biocompatible material according to the embodiment of the present invention. In a case where the content of the oil-based base material is within this range, the effects obtained by the biocompatible material according to the embodiment of the present invention including the oil-based base material are further exhibited.

Further, in the biocompatible material according to the embodiment of the present invention, the value of the ratio (mass ratio) [mass of alginate/mass of oil-based base material] of the content of the alginate to the content of the oil-based base material is not particularly limited; however, in many cases, it is 0.10 to 0.70, and is preferably 0.10 to 0.50, more preferably 0.20 to 0.50, and still more preferably 0.20 to 0.40 since the excellent scratch resistance of the formed gel is more excellent and the spreadability and adhesivity of the biocompatible material is more excellent.

The biocompatible material according to the embodiment of the present invention is substantially free of water. "Substantially free of water" means that it is acceptable to contain a small amount of water (for example, a trace amount of water contained in the raw material) that does not affect the effects of the present invention. Specifically, "substantially free of water" means that the content of water in the biocompatible material according to the embodiment of the present invention is 5% by mass or less with respect to the total mass of the biocompatible material according to the embodiment of the present invention. Among the above range, 3% by mass or less is preferable. The lower limit is not particularly limited; however, 0% by mass can be mentioned.

In a case where the biocompatible material according to the embodiment of the present invention is substantially free of water, the attachability of the gel that is formed when the biocompatible material according to the embodiment of the present invention is applied to a living body is further improved, and the protective performance is also improved. In addition, the storage stability of the biocompatible material according to the embodiment of the present invention is further improved.

The method for measuring the content of water in the biocompatible material according to the embodiment of the present invention is preferably the Karl Fischer water content measuring method is preferable. The measurement conditions are described in JIS K0068: 2001.

The biocompatible material according to the embodiment of the present invention may contain components other than those described above.

<Sugar Alcohol and Sugar>

The biocompatible material according to the embodiment according to the embodiment of the present invention may further contain at least one selected from the group consisting of a sugar alcohol and a sugar. In a case where the biocompatible material according to the embodiment of the present invention contains at least one selected from the group consisting of a sugar alcohol and a sugars, scratch resistance is more excellent when the biocompatible material is gelated.

<Kind of Sugar Alcohol>

The sugar alcohol is an organic compound having a structure in which the carbonyl group of aldose or ketose is reduced, and specific examples thereof include erythritol, xylitol, mannitol, and sorbitol, and at least one selected from the group consisting of erythritol, xylitol, mannitol, and sorbitol is preferable, and xylitol is more preferable.

<<Kind of Sugar>>

The sugar is not particularly limited; however, examples thereof include a monosaccharide and a disaccharide, and specific examples thereof include glucose, galactose, sucrose, trehalose, and lactose, and at least one selected from the group consisting of glucose and galactose is preferable, and trehalose is more preferable.

The at least one selected from the group consisting of a sugar alcohol and a sugar is preferably at least one selected from the group consisting of erythritol, xylitol, mannitol, sorbitol, glucose, galactose, sucrose, trehalose, and lactose.

<Content of Sugar Alcohol and Sugar>

The total content of the sugar alcohol and the sugar in the biocompatible material according to the embodiment of the present invention in a case where the biocompatible material according to the embodiment of the present invention contains at least one selected from the group consisting of a sugar alcohol and a sugar is not particularly limited; however, it is preferably 0.5% by mass to 20.0% by mass and more preferably 5.0% by mass to 15.0% by mass, with respect to the total mass of the biocompatible material according to the embodiment of the present invention. In a case where the total content of the sugar alcohol and the sugar is within this range, the effects obtained by the biocompatible material according to the embodiment of the present invention including at least one selected from the group consisting of a sugar alcohol and a sugar is further exhibited.

<Method for Manufacturing Biocompatible Material>

The biocompatible material according to the embodiment of the present invention is manufactured by mixing an alginate having a weight-average molecular weight of 1 million or more, an aluminum compound, a carboxyvinyl polymer, and an oil-based base material. As necessary, dehydration treatment may be carried out.

The mixing method is not particularly limited, and a conventionally known method used when mixing powder components can be used.

For example, a stepwise mixing method in which a part of components constituting the biocompatible material is mixed in advance and then mixed with the remaining components may be carried out. Among the components, in a case where at least one selected from the group consisting of a sugar alcohol and a sugar is used, an alginate having a weight-average molecular weight of 1 million or more, an aluminum compound, a carboxyvinyl polymer, and the one selected from the group consisting of a sugar alcohol and a sugar are mixed to obtain a mixture, and subsequently, the mixture is preferably mixed with an oil-based base material. According to the above procedure, a biocompatible material in which components are more uniformly dispersed can be obtained.

In a case where the above mixture and the oil-based base material are mixed, the mixture may be mixed with the oil-based base material in one batch, or the mixture may be added to the oil-based base material in a plurality of times and mixed.

After mixing each component, the obtained biocompatible material is preferably degassed to remove water from the biocompatible material.

<Function of Biocompatible Material>

A gel having a crosslinked structure is formed by bringing the biocompatible material according to the embodiment of the present invention into contact with water. More specifically, in a case where the biocompatible material according to the embodiment of the present invention is brought into contact with water, a gel including a crosslinked structure formed by crosslinking an alginate with an aluminum compound is formed. In addition, in a case where the biocompatible material according to the embodiment of the present invention includes at least one selected from the group consisting of a sugar alcohol and a sugar, a gel including two kinds of crosslinked structures of a first crosslinked structure formed by crosslinking an alginate with an aluminum compound and a second crosslinked structure formed by crosslinking a carboxyvinyl polymer with at least one selected from the group consisting of a sugar alcohol and a sugar. That is, the biocompatible material according to the embodiment of the present invention absorbs water to spontaneously form a crosslinked structure.

The biocompatible material according to the embodiment of the present invention can be applied onto the biological surface to form a gel. As a method for forming a gel, a method in which the biocompatible material according to the embodiment of the present invention is placed on the biological surface, and the biocompatible material placed on the biological surface is brought into contact with water to form a gel on the biological surface is mentioned.

As the biological surface on which the biocompatible material according to the embodiment of the present invention is placed, the mucous membrane surface in the oral cavity is preferably mentioned.

The viscosity of the biocompatible material according to the embodiment of the present invention is not particularly limited; however, in many cases, it is 100,000 to 600,000 cP, and is preferably 20,000 to 500,000 cP since the biocompatible material according to the embodiment of the present invention has more excellent spreadability and adhesivity. The viscosity is measured using a viscoelasticity measuring device (MCR302) at a measurement temperature of 25° C. and a shear rate of 1 (1/s).

The form (shape) of the biocompatible material according to the embodiment of the present invention is not particularly limited; however, examples thereof include an ointment, a cream, and a semi-solid.

<Use and Method for Using Biocompatible Material>

As the use of the biocompatible material according to the embodiment of the present invention, use for living body protection is mentioned, which is not limited to.

Specifically, the biocompatible material according to the embodiment of the present invention can be used, for example, as a mucous membrane protective agent, and more specifically, as an oral cavity mucous membrane protective agent.

Further, the biocompatible material according to the embodiment of the present invention is also used for a wound dressing material, a drug sustainedly-releasing base material, an oral cavity wetting material, and a hemostatic material.

In a case where the biocompatible material according to the embodiment of the present invention is used for a mucous membrane, when the biocompatible material according to the embodiment of the present invention is placed on the mucous membrane and water or a solution containing water is added, a gel that is formed by gelation more strongly attaches to the mucous membrane. That is, as a method (or a method for manufacturing a gel) of using the biocompatible material according to the embodiment of the present invention, a method in which the biocompatible material according to the embodiment of the present invention is placed on the mucous membrane, and the biocompatible material placed on the mucous membrane is brought into contact with water to form a gel on the mucous membrane is mentioned.

In particular, in a case where the biocompatible material according to the embodiment of the present invention is applied to the oral cavity mucous membrane, when the biocompatible material according to the embodiment of the present invention is attached to the oral cavity mucous membrane, the biocompatible material according to the embodiment of the present invention is gelated by the water in saliva, and thus is handling is easy. In addition, in a case where the amount of saliva is small, water or artificial saliva may be sprayed to supply water after the biocompatible material according to the embodiment of the present invention is attached to the oral cavity mucous membrane.

In a case where the biocompatible material according to the embodiment of the present invention is attached to the oral cavity mucous membrane, the formation of the cross-linked structure is initiated by the water in saliva, and at the same time, mucin and an alginate on the surface of the oral cavity mucous membrane are adhered by hydrogen bonds. By such a mechanism, the gel that is formed by the biocompatible material according to the embodiment of the present invention is presumed to exhibit excellent scratch resistance and excellent retention, but the mechanism is not limited thereto.

In a case where the biocompatible material according to the embodiment of the present invention is used as a drug sustainedly-releasing base material, the kind of the drug that is sustainedly released is not particularly limited, and known drugs are mentioned.

EXAMPLES

Hereinafter, the present invention will be more specifically described according to Examples, but the present invention is not limited to these Examples.

Examples 1 to 30 and Comparative Examples 1 to 10

<Preparation of Biocompatible Material>

Each component shown in Table 1 was mixed at the content shown in Table 1 to prepare biocompatible materials of Examples 1 to 30 and Comparative Examples 1 to 10.

In all cases, the content of water in the biocompatible materials prepared in Examples 1 to 30 and Comparative Examples 1 to 10 was 3% by mass or less with respect to the total mass of the biocompatible materials. That is, all of the biocompatible materials of Examples were substantially free of water.

The procedure for manufacturing the biocompatible material of Example 1 is representatively described below. In other Examples and Comparative Examples, the amount of each component used was adjusted and the manufacture was carried out in the same procedure.

Example 1

324 g of sodium alginate (manufactured by KIMICA Corporation, KIMICA ALGIN I-S, 36 g of aluminum lactate (manufactured by Musashino Chemical Laboratory, Ltd.). 180 g of xylitol (manufactured by Mitsubishi Corporation Life Sciences Limited, Xylit P), and 180 g of a carboxyvinyl polymer (Lubrizol Corporation, CARBOPOL 971P NF) were uniformly powder-mixed and divided into three aliquots.

3,500 g of liquid paraffin (manufactured by Kaneda Co., Ltd., HICALL M-352) and 3,500 g of an ointment base Plastibase (manufactured by Taisho Pharmaceutical Co., Ltd.) were uniformly mixed, and the mixture was filtered through a nylon mesh (manufactured by NBC Meshtec Inc., N-NO. 230T). 1,080 g of the obtained mixture was charged into HIVIS DISPER MIX 3D-5 type (manufactured by Primix Corporation), and with stirring at 20° C. with a planetary mixer of 5 rpm (without using Homo Disper) (hereinafter, stirring was continued under the same stirring conditions), the powder divided into three aliquots was added sequentially. The addition of each powder took 1 minute, and after the addition, the mixture was stirred for 1 minute.

When 1 minute passed after the completion of the final addition, the inside of the system was vacuum degassed and stirring was continued for another 20 minutes to obtain the biocompatible material (1,800 g) of Example 1. 7 g of the obtained biocompatible material was filled in each aluminum tube (manufactured by Kansai Tube Co., Ltd.) and stored at room temperature until use.

<Performance Evaluation>

<<Preparation of Pseudo Biological Membrane>>

Tetradodecyl ammonium bromide (TDAB, manufactured by FUJIFILM Wako Pure Chemical Corporation; 50 mg), polyvinyl chloride (manufactured by FUJIFILM Wako Pure Chemical Corporation; 800 mg), and di-n-octylphosphonate (DOPP, manufactured by FUJIFILM Wako Pure Chemical Corporation; 0.6 mL) were dissolved in tetrahydrofuran (THF, FUJIFILM Wako Pure Chemical Corporation; 10 mL) and dried at room temperature with a petri dish to obtain a lipid membrane (about 200 µm thickness).

Next, the prepared lipid membrane was attached to a hygrogel formed of agar (Karikorikan (registered trade mark), manufactured by Ina Food Industry Co., Ltd.; 0.5 g), gellan gum (Kelcogel (registered trade mark), manufactured by CP Kelco; 0.1 g), and distilled water (49.4 g).

Subsequently, the surface of the lipid membrane was coated with a 2-methacryloyloxyethyl phosphorylcholine (MPC) polymer (LIPIDURE (registered trade mark)—CM5206, manufactured by NOF CORPORATION) to obtain a pseudo biological membrane.

<<Evaluation of Scratch Resistance>>

The prepared biocompatible material was applied onto the prepared pseudo biological membrane (1 any, 500 μm thickness), artificial saliva (Saliveht (registered trade mark), manufactured by TEIJIN PHARMA LIMITED) was sprayed thereon, and then the sample was allowed to stand for 1 minute for gelation to prepare a sample for evaluation.

The prepared evaluation sample was repeatedly worn with a wear testing machine (surface property measuring machine Tribogear TYPE: 14FW, manufactured by Shinto Scientific Co., Ltd.), and the times of the reciprocation until the sample was peeled or dissolved from the pseudo biological membrane was measured, and scratch resistance was evaluated according to the following criteria. A triangular eraser core (Ain CLIC, manufactured by Pentel Co, Ltd) was set on the head of the wear testing machine, and the test was performed under the conditions of a load of 30 g, an amplitude of 30 mm, and a speed of 6,000 mm/min.

(Evaluation of Scratch Resistance)

Endured more than 700 times . . . S

Peeled after 500 times or more and less than 700 times . . . A

Peeled after 100 times or more and less than 500 times . . . B

Peeled after less than 100 times . . . C

The evaluation results are shown in the "Evaluation" column of Table 1.

<<Evaluation of Retention>>

The prepared biocompatible material was applied onto the prepared pseudo biological membrane (1 cmφ, 500 μm thickness), artificial saliva (Saliveht (registered trade mark), manufactured by TEIJIN PHARMA LIMITED) was sprayed thereon, and then the sample was allowed to stand for 1 minute for gelation to prepare a sample for evaluation.

The prepared evaluation sample was placed in a petri dish and filled with artificial saliva (Saliveht (registered trade mark), manufactured by TEIJIN PHARMA LIMITED) until the evaluation sample was immersed. This petri dish was placed in a constant temperature shaker (small shaking incubator manufactured by AS ONE Corporation, 1-6142-01) (37° C.) and shaken at a medium speed (scale 6). In this test, the time required for the evaluation sample to disappear by being peeled or dissolved from the pseudo biological membrane was measured, and the retention was evaluated according to the following criteria.

(Evaluation Criteria for Retention)

Retained for 4 hours or more . . . S

Disappeared in 2 hours or more and less than 4 hours . . . A

Disappeared in 1 hours or more and less than 2 hours . . . B

Disappeared in less than 4 hours . . . C

The evaluation results are shown in the "Evaluation" column of Table 1.

<<Evaluation of Spreadability and Adhesivity>>

The viscosity of the prepared biocompatible material was measured using a viscoelasticity measuring device (MCR302) at a measurement temperature of 25° C. and a shear rate of 1 (1/s), and the spreadability and adhesivity was evaluated according to the following criteria.

(Evaluation Criteria for Spreadability and Adhesivity)

The viscosity value at a shear rate of 1 s$^{-1}$ was 500,000 cP or less . . . A The viscosity value at a shear rate of 1 s$^{-1}$ was more than 500,000 cP . . . B

TABLE 1-1

| | | (1/4) Examples | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Component (I) | Alginate (1) | 18.0 | | | | 18.0 | 18.0 | 9.0 | 27.0 | 18.0 | 19.3 | 16.0 | 18.0 |
| | Alginate (2) | | | | | | | | | | | | |
| | Alginate (3) | | | | | | | | | | | | |
| | Alginate (4) | | 18.0 | | | | | | | | | | |
| | Alginate (5) | | | 18.0 | 18.0 | | | | | | | | |
| | Alginate (6) | | | | | | | | | | | | |
| | Alginate (7) | | | | | | | | | | | | |
| | Alginate (8) | | | | | | | | | | | | |
| Component (II) | Aluminum compound (1) | 2.0 | 2.0 | 2.0 | 2.0 | 2.0 | 2.0 | 1.0 | 3.0 | | 0.7 | 4.0 | 2.0 |
| | Aluminum compound (2) | | | | | | | | | 2.0 | | | |
| | Calcium compound | | | | | | | | | | | | |
| | Iron (II) compound | | | | | | | | | | | | |
| Component (III) | Carboxyvinyl polymer (1) | 10.0 | 10.0 | 10.0 | 10.0 | 10.0 | 10.0 | 15.0 | 5.0 | 10.0 | 10.0 | 10.0 | |
| | Carboxyvinyl polymer (2) | | | | | | | | | | | | 10.0 |
| | Sodium polyacrylate | | | | | | | | | | | | |

TABLE 1-1-continued (1/4)

| | | Examples | | | | | | | | | | | |
|---|---|---|---|---|---|---|---|---|---|---|---|---|
| | | 1 | 2 | 3 | 4 | 5 | 6 | 7 | 8 | 9 | 10 | 11 | 12 |
| Component (IV) | Xylitol | 10.0 | 10.0 | 10.0 | 10.0 | 10.0 | 10.0 | 15.0 | 5.0 | 10.0 | 10.0 | 10.0 | 10.0 |
| | Erythritol | | | | | | | | | | | | |
| | Mannitol | | | | | | | | | | | | |
| | Sorbitol | | | | | | | | | | | | |
| | Glucose | | | | | | | | | | | | |
| | Galactose | | | | | | | | | | | | |
| | Sucrose | | | | | | | | | | | | |
| | Lactose | | | | | | | | | | | | |
| | Trehalose | | | | | | | | | | | | |
| Component (V) | Plastibase | 30.0 | 30.0 | 30.0 | 30.0 | 30.0 | 30.0 | 30.0 | 30.0 | 30.0 | 30.0 | 30.0 | 30.0 |
| | Liquid paraffin | 30.0 | 30.0 | 30.0 | 30.0 | 30.0 | 30.0 | 30.0 | 30.0 | 30.0 | 30.0 | 30.0 | 30.0 |
| | Total | 100.0 | 100.0 | 100.0 | 100.0 | 100.0 | 100.0 | 100.0 | 100.0 | 100.0 | 100.0 | 100.0 | 100.0 |
| Mass of Component (I)/ Mass of Component (III) | | 1.8 | 1.8 | 1.8 | 1.8 | 1.8 | 1.8 | 0.6 | 5.4 | 1.8 | 1.9 | 1.6 | 1.8 |
| Mass of Component (I)/ Mass of Component (V) | | 0.30 | 0.30 | 0.30 | 0.30 | 0.30 | 0.30 | 0.15 | 0.45 | 0.30 | 0.32 | 0.27 | 0.30 |
| Evaluation | Scratch resistance | S | B | B | B | S | A | B | A | A | A | S | B |
| | Retention | S | S | S | S | S | S | S | S | B | A | S | B |
| | Spreadability and adhesivity | A | A | A | A | A | A | A | A | A | A | A | A |

The content of each component is indicated in terms of parts by mass.

TABLE 1-2

(2/4)

| | | Examples | | | | | | | | | | | |
|---|---|---|---|---|---|---|---|---|---|---|---|---|
| | | 13 | 14 | 15 | 16 | 17 | 18 | 19 | 20 | 21 | 22 | 23 | 24 | 25 |
| Component (I) | Alginate (1) | 18.0 | 18.0 | 18.0 | 18.0 | 18.0 | 18.0 | 18.0 | 18.0 | 18.0 | 24.0 | 21.0 | 14.0 | 8.0 |
| | Alginate (2) | | | | | | | | | | | | | |
| | Alginate (3) | | | | | | | | | | | | | |
| | Alginate (4) | | | | | | | | | | | | | |
| | Alginate (5) | | | | | | | | | | | | | |
| | Alginate (6) | | | | | | | | | | | | | |
| | Alginate (7) | | | | | | | | | | | | | |
| | Alginate (8) | | | | | | | | | | | | | |
| Component (II) | Aluminum compound (1) | 2.0 | 2.0 | 2.0 | 2.0 | 2.0 | 2.0 | 2.0 | 2.0 | 2.0 | 2.0 | 2.0 | 2.0 | 2.0 |
| | Aluminum compound (2) | | | | | | | | | | | | | |
| | Calcium compound | | | | | | | | | | | | | |
| | Iron (II) compound | | | | | | | | | | | | | |
| Component (III) | Carboxyvinyl polymer (1) | 10.0 | 10.0 | 10.0 | 10.0 | 10.0 | 10.0 | 10.0 | 10.0 | 10.0 | 4.0 | 7.0 | 14.0 | 20.0 |
| | Carboxyvinyl polymer (2) | | | | | | | | | | | | | |
| | Sodium polyacrylate | | | | | | | | | | | | | |
| Component (IV) | Xylitol | 10.0 | 10.0 | | | | | | | | 10.0 | 10.0 | 10.0 | 10.0 |
| | Erythritol | | | | | | | | | | | | | |
| | Mannitol | | | | | | | | | | | | | |
| | Sorbitol | | | 10.0 | | 10.0 | 10.0 | | | | | | | |
| | Glucose | | | | | | | | | | | | | |
| | Galactose | | | | | | | | | | | | | |
| | Sucrose | | | | | | | 10.0 | 10.0 | 10.0 | | | | |
| | Lactose | | | | | | | | | | | | | |
| | Trehalose | | | | | | | | | | | | | |

TABLE 1-2-continued (2/4) Examples

| | | 13 | 14 | 15 | 16 | 17 | 18 | 19 | 20 | 21 | 22 | 23 | 24 | 25 |
|---|---|---|---|---|---|---|---|---|---|---|---|---|---|---|
| Component (V) | Plastibase | 30.0 | 30.0 | 30.0 | 35.0 | 30.0 | 30.0 | 30.0 | 30.0 | 30.0 | 30.0 | 30.0 | 30.0 | 30.0 |
| | Liquid paraffin | 30.0 | 30.0 | 30.0 | 35.0 | 30.0 | 30.0 | 30.0 | 30.0 | 30.0 | 30.0 | 30.0 | 30.0 | 30.0 |
| | Total | 100.0 | 100.0 | 100.0 | 100.0 | 100.0 | 100.0 | 100.0 | 100.0 | 100.0 | 100.0 | 100.0 | 100.0 | 100.0 |
| Mass of Component (I)/ Mass of Component (III) | | 1.8 | 1.8 | 1.8 | 1.8 | 1.8 | 1.8 | 0.6 | 5.4 | 1.8 | 6.0 | 3.0 | 1.0 | 0.4 |
| Mass of Component (I)/ Mass of Component (V) | | 0.30 | 0.30 | 0.30 | 0.26 | 0.30 | 0.30 | 0.15 | 0.45 | 0.30 | 0.40 | 0.35 | 0.23 | 0.13 |
| Evaluation | Scratch resistance | A | S | S | B | S | S | S | S | S | A | A | A | B |
| | Retention | S | S | S | S | S | S | S | S | S | B | A | A | B |
| | Spreadability and adhesivity | A | A | A | A | A | A | A | A | A | A | A | A | A |

The content of each component is indicated in terms of parts by mass.

TABLE 1-3

(3/4) Examples

| | | 26 | 27 | 28 | 29 | 30 |
|---|---|---|---|---|---|---|
| Component (I) | Alginate (1) | 18.0 | 18.0 | 18.0 | 9.0 | 27.0 |
| | Alginate (2) | | | | | |
| | Alginate (3) | | | | | |
| | Alginate (4) | | | | | |
| | Alginate (5) | | | | | |
| | Alginate (6) | | | | | |
| | Alginate (7) | | | | | |
| | Alginate (8) | | | | | |
| Component (II) | Aluminum compound (1) | 2.0 | 2.0 | 2.0 | 1.0 | 3.0 |
| | Aluminum compound (2) | | | | | |
| | Calcium compound | | | | | |
| | Iron (II) compound | | | | | |
| Component (III) | Carboxyvinyl polymer (1) | 10.0 | 10.0 | 10.0 | 5.0 | 15.0 |
| | Carboxyvinyl polymer (2) | | | | | |
| | Sodium polyacrylate | | | | | |
| Component (IV) | Xylitol | 10.0 | 10.0 | 10.0 | 5.0 | 15.0 |
| | Erythritol | | | | | |
| | Mannitol | | | | | |
| | Sorbitol | | | | | |
| | Glucose | | | | | |
| | Galactose | | | | | |
| | Sucrose | | | | | |
| | Lactose | | | | | |
| | Trehalose | | | | | |
| Component (V) | Plastibase | | | 30.0 | 40.0 | 20.0 |
| | Liquid paraffin | 30.0 | 30.0 | | 40.0 | 20.0 |
| | HICALL GEL | | | | | |
| | White vaseline | | 30.0 | 30.0 | | |
| | Olive oil | | | | | |
| | Total | 100.0 | 100.0 | 100.0 | 100.0 | 100.0 |
| Mass of Component (I)/ Mass of Component (III) | | 1.8 | 1.8 | 1.8 | 1.8 | 1.8 |
| Mass of Component (I)/ Mass of Component (V) | | 0.30 | 0.30 | 0.30 | 0.11 | 0.68 |
| Evaluation | Scratch resistance | S | A | S | B | S |
| | Retention | S | S | S | A | S |
| | Spreadability and adhesivity | A | A | A | A | B |

The content of each component is indicated in terms of parts by mass.

TABLE 1-4

(4/4) Comparative Examples

| | | 1 | 2 | 3 | 4 | 5 | 6 | 7 | 8 | 9 | 10 |
|---|---|---|---|---|---|---|---|---|---|---|---|
| Component (I) | Alginate (1) | | | | 36.0 | 18.0 | 18.0 | 20.0 | 18.0 | 18.0 | 20.0 |
| | Alginate (2) | | | | | | | | | | |
| | Alginate (3) | | | | | | | | | | |
| | Alginate (4) | | | | | | | | | | |
| | Alginate (5) | 18.0 | 18.0 | | | | | | | | |
| | Alginate (6) | | | | | | | | | | |
| | Alginate (7) | | | | | | | | | | |
| | Alginate (8) | | | | | | | | | | |

TABLE 1-4-continued (4/4)
Comparative Examples

| | | 1 | 2 | 3 | 4 | 5 | 6 | 7 | 8 | 9 | 10 |
|---|---|---|---|---|---|---|---|---|---|---|---|
| Component (II) | Aluminum compound (1) | 2.0 | 2.0 | | 4.0 | | | | 2.0 | 2.0 | |
| | Aluminum compound (2) | | | | | | | | | | |
| | Calcium compound | | | | | 2.0 | 2.0 | | | | |
| | Iron (II) compound | | | | | | | | | | |
| Component (III) | Carboxyvinyl polymer (1) | 10.0 | 10.0 | 20.0 | | 10.0 | 10.0 | 10.0 | | | 30.0 |
| | Carboxyvinyl polymer (2) | | | | | | | | | 10.0 | |
| | Sodium polyacrylate | | | | | | | | | | |
| Component (IV) | Xylitol | 10.0 | 10.0 | 20.0 | | 10.0 | 10.0 | 10.0 | 10.0 | 10.0 | |
| | Erythritol | | | | | | | | | | |
| | Mannitol | | | | | | | | | | |
| | Sorbitol | | | | | | | | | | |
| | Glucose | | | | | | | | | | |
| | Galactose | | | | | | | | | | |
| | Sucrose | | | | | | | | | | |
| | Lactose | | | | | | | | | | |
| | Trehalose | | | | | | | | | | |
| Component (V) | Plastibase | 30.0 | 30.0 | 30.0 | 30.0 | 30.0 | 30.0 | 30.0 | 35.0 | 30.0 | 25.0 |
| | Liquid paraffin | 30.0 | 30.0 | 30.0 | 35.0 | 30.0 | 30.0 | 30.0 | 35.0 | 30.0 | 25.0 |
| | Total | 100.0 | 100.0 | 100.0 | 100.0 | 100.0 | 100.0 | 100.0 | 100.0 | 100.0 | 100.0 |
| Mass of Component (I)/Mass of Component (III) | | 1.8 | 1.8 | 0.0 | | 1.8 | 1.8 | 2.0 | | | 0.7 |
| Mass of Component (I)/Mass of Component (V) | | 0.30 | 0.30 | 0.00 | 0.60 | 0.30 | 0.30 | 0.33 | 0.26 | 0.30 | 0.40 |
| Evaluation | Scratch resistance | C | C | C | B | B | B | B | C | B | B |
| | Retention | A | A | A | C | C | C | C | B | C | C |
| | Spreadability and adhesivity | A | A | A | A | A | A | A | A | A | A |

The content of each component is indicated in terms of parts by mass.

Components I to III and component V in Table 1 are as described below. Here, Mw represents a weight-average molecular weight.

<Component I>

Alginate (1)
Sodium alginate, KIMICA ALGIN I-S (manufactured by KIMICA Corporation) Mw=4.05 million, average particle size=174 μm Alginate (2)
Sodium alginate, KIMICA ALGIN I-S (manufactured by KIMICA Corporation) Mw=4.05 million, average particle size=138 μm Alginate (3)
Sodium alginate, KIMICA ALGIN I-S (manufactured by KIMICA Corporation) Mw=4.05 million, average particle size=51 μm Alginate (4)
Sodium alginate, KIMICA ALGIN I-8 (manufactured by KIMICA Corporation) Mw=3.90 million, average particle size=60 μm Alginate (5)
Sodium alginate, KIMICA ALGIN I-5 (manufactured by KIMICA Corporation) Mw=3.04 million, average particle size=102 μm Alginate (6)
Sodium alginate, KIMICA ALGIN I-3 (manufactured by KIMICA Corporation) Mw=2.75 million, average particle size=64 μm Alginate (7)
Sodium alginate, KIMICA ALGIN I-1 (manufactured by KIMICA Corporation) Mw=0.78 million, average particle size=117 μm Alginate (8)
Sodium alginate, KIMICA ALGIN ULV-L3 (manufactured by KIMICA Corporation) Mw=50 thousand, average particle size=78 μm <Component II>

Aluminum compound (1)
Aluminum lactate

Aluminum compound (2)
$AlK(NH_4)(SO_4)_2 \cdot 12H_2O$

Calcium compound Calcium lactate

Iron (II) compound
Iron lactate (II)

<Component III>

Carboxyvinyl polymer (1)
CARBOPOL (registered trade mark) 971P NF (manufactured by Lubrizol Corporation)
Viscosity of 0.5% by mass of an aqueous solution at pH 7.5 and 25° C.: 15,700 cP Carboxyvinyl polymer (2)
AQUPEC (registered trade mark) HV805 (manufactured by SUMITOMO SEIKA CHEMICALS CO., LTD.)
Viscosity of 0.5% by mass of an aqueous solution at pH 7.5 and 25° C.: 56,400 cP Sodium polyacrylate Sodium polyacrylate (FUJIFILM Wako Pure Chemical Corporation)

<Component V>

Plastibase (manufactured by Taisho Pharmaceutical Co., Ltd.)

Liquid paraffin (manufactured by KANEDA Co., Ltd., HICALL M-352)

HICALL GEL (manufactured by KANEDA Co., Ltd.)

White vaseline (manufactured by TOYO Pharmaceutical Co., Ltd.)

Olive oil (manufactured by FUJIFILM Wako Pure Chemical Corporation)

[Explanation of Result]

The biocompatible materials of Examples 1 to 30 had an evaluation of S to B in both scratch resistance and retention and were excellent in both scratch resistance and retention.

On the other hand, in the biocompatible materials of Comparative Examples 1 to 10, at least one of scratch resistance or retention was an evaluation of C, and at least one of scratch resistance or retention was inferior.

In Example 1, Example 5, and Example 6 in which the weight-average molecular weight of alginate were 4 million or more, scratch resistance was excellent as compared with Example 2, Example 3, and Example 4 in which the weight-average molecular weight of alginate was less than 4 million.

In Examples 1 and 5 in which the average particle size of the particles of the alginate is in the range of 110 μm or more and less than 200 μm, scratch resistance was excellent as compared with Examples 2 to 4 and Example 6 in which the average particle size of the particles of the alginate was out of the range of 110 μm or more and less than 200 μm.

In Examples 1 and 8 in which the content of the alginate was in the range of 10.0% by mass to 30.0% by mass with respect to the total mass of the biocompatible material, scratch resistance was excellent as compared with Example 7 in which was the content of the alginate was less than 10.0% by mass with respect to the total mass of the biocompatible material.

In Example 1 in which aluminum lactate was used as an aluminum compound, retention was excellent as compared with Example 9 in which ammonium alum (Na(NH$_4$).(SO$_4$)$_2$.12H$_2$O) was used.

In Examples 1 and 11 in which the content of the aluminum compound is in the range of 1.0% by mass to 4.5% by mass with respect to the total mass of the biocompatible material, retention was excellent as compared with Example 10 in which the content thereof was out of the range.

In Example 1 in which a viscosity of a 0.5% by mass of aqueous solution (25° C.) of a carboxyvinyl polymer at pH 7.5 is 20,000 cP or less, both the scratch resistance and the retention were excellent as compared with Example 12 in which the viscosity was more than 20,000 cP.

In Example 1, Examples 13 to 15, and Examples 17 to 21, including a sugar alcohol, scratch resistance was excellent as compared with Example 16, not including both a sugar alcohol and a sugar.

In Example 1, Example 7, Example 8, Example 10, Example 11, and Examples 23 to 24, in which the value of the ratio (mass ratio) [content of alginate/content of carboxyvinyl polymer] of the content of the alginate to the content of the carboxyvinyl polymer was in the range of 0.5 to 5.5, retention was more excellent. In Example 1, Example 8, Example 10, Example 11, and Examples 23 to 24, in which the value was in the range of 1.0 to 5.5, scratch resistance was more excellent in addition to retention.

From the comparison of Examples 26 to 28, it has been confirmed that in a case where a combination of a gelated hydrocarbon and liquid paraffin or a combination of a gelated hydrocarbon and a vegetable oil is used as an oil-based base material, more excellent effects can be obtained.

From the comparison of Examples 29 to 30 with other Examples, it has been confirmed that in a case where the content of the oil-based base material is 50% by mass to 70% by mass with respect to the total mass of the biocompatible material according to the embodiment of the present invention, more excellent effects can be obtained.

From the comparison of Example 1 and Example 7 with Example 29 and Example 30, it has been confirmed that in a case where the value of the ratio of the content of the alginate to the content of the oil-based base material is 0.20 to 0.50, more excellent effects can be obtained.

Example 31: Confirmation of Stomatitis Protective Effect by Stomatitis Model Mouse (Part 1)

An animal experiment was carried out using a stomatitis model mouse for the purpose of confirming the stomatitis protection function of the biocompatible material according to the embodiment of the present invention. The stomatitis model mouse referred to here is a mouse in which stomatitis is artificially developed, and it is known that such a mouse cannot take sufficient food due to pain, which results in body weight loss or death from starvation (Reference: "Ito's Toxicologic Pathology" edited by Michito Takahashi and Shoji Fukushima, Maruzen Publishing (published Jul. 30, 2013) (ISBN978-4-621-08642-1C3047), 6. Toxic pathology of target organs, 6. 4. Oral cavity, tongue, pharynx, P195 "6.4.5 Influence of damage").

The degree of stomatitis was changed as below, and the protective effect against stomatitis was checked from the number of surviving mice and the change in body weight of each mouse.

Six-week-old mice (C57BL/6) were purchased from The Jackson Laboratories, and after preliminary breeding including the quarantine period for one-week, mice (8 mice) having no abnormalities in the general state were selected, and randomly divided into 2 groups (4 mice each) of a group A and a group B.

The mice in each group were anesthetized with isoflurane, the tongue, and the mucous membrane surface in the oral cavity were exposed to a 20% acetic acid aqueous solution exuded from a 2 mm filter paper for 1 minute and then washed with phosphate buffered saline to develop stomatitis.

The mice in the group A were bred for 8 days while applying the biocompatible material (300 μg) of Example 1 according to the embodiment of the present invention to the wound part (stomatitis) twice a day.

The mice in the group B were bred in the same manner for 8 days, except that the biocompatible material according to the embodiment of the present invention was replaced with phosphate buffered saline.

In the group A (Example), three mice survived, and in the group B (Comparative Example) one mouse survived. From this result, it was confirmed that the biocompatible material according to the embodiment of the present invention functions effectively as an oral cavity mucous membrane protective agent.

Example 32: Confirmation of Stomatitis Protective Effect by Stomatitis Model Mouse (Part 2)

Six-week-old mice (C57BL/6) were purchased from The Jackson Laboratories, and after preliminary breeding including the quarantine period for one-week, mice (6 mice) having no abnormalities in the general state were selected, and randomly divided into 2 groups (3 mice each) of a group C and a group D.

The mice in each group were anesthetized with isoflurane, the tongue, and oral cavity mucous membrane surface were exposed to a 10% acetic acid aqueous solution exuded from a 2 mm filter paper for 1 minute and then washed with phosphate buffered saline to develop stomatitis.

The mice in the group C were bred for 8 days while applying the biocompatible material (300 µg) of Example 1 according to the embodiment of the present invention to the wound part (stomatitis) twice a day. In addition, the body weight of each mouse was measured daily, and the average value thereof was calculated.

The mice in the group D were bred in the same manner for 8 days, except that the biocompatible material according to the embodiment of the present invention was replaced with phosphate buffered saline. In addition, the body weight of each mouse was measured daily, and the average value thereof was calculated.

There were no deaths of mice both in the C group (Example) or the D group. The increase of body weight of the mice in the group C was confirmed from the day after the treatment with the 10% acetic acid aqueous solution, and an average increase of body weight of 3 g was observed when 8 days passed after the treatment. On the other hand, no clear increase in body weight was observed in the mice of the D group during the breeding period for 8 days.

From the animal experiments shown in Examples 31 and 32 described above, it has been confirmed that the biocompatible material according to the embodiment of the present invention has an excellent function of protecting the mucous membrane in the stomatitis state.

Example 33

The performance of astaxanthin as a sustainedly-releasing base material in the oral cavity was evaluated.

A dark red biocompatible material A was obtained in the same manner as in Example 1, except that each of the contents of Plastibase and liquid paraffin of the formulation of Example 1 was changed from 30 parts by mass to 25 parts by mass and instead, 10 parts by mass of ASTOTS-S (FUJIFILM Holdings Corporation) was added.

Using an evaluation system for retention, the sustainedly-releasing performance of astaxanthin of the biocompatible material A was evaluated under the conditions simulating an environment of the inside of the oral cavity. From the result, it has been confirmed that artificial saliva continues to be colored to a red color derived from the astaxanthin for 3 hours immediately after being immersed in the artificial saliva.

From these results, it has been shown that the biocompatible material according to the embodiment of the present invention has a function of sustainedly releasing a component such as astaxanthin in an environment such as the inside of the oral cavity.

What is claimed is:

1. A biocompatible material comprising:
    an alginate having a weight-average molecular weight of 1 million or more;
    an aluminum compound;
    a carboxyvinyl polymer; and
    an oil-based base material,
    wherein the biocompatible material is substantially free of water.

2. The biocompatible material according to claim 1, further comprising:
    at least one selected from the group consisting of a sugar alcohol and a sugar.

3. The biocompatible material according to claim 2, wherein the at least one selected from the group consisting of a sugar alcohol and a sugar is at least one selected from the group consisting of erythritol, xylitol, mannitol, sorbitol, glucose, galactose, sucrose, trehalose, and lactose.

4. The biocompatible material according to claim 1, wherein the alginate is at least one selected from the group consisting of sodium alginate, potassium alginate, and ammonium alginate.

5. The biocompatible material according to claim 1, wherein the alginate has a weight-average molecular weight of 2 million or more.

6. The biocompatible material according to claim 1, wherein the alginate has a weight-average molecular weight of 3 million or more.

7. The biocompatible material according to claim 1, wherein the alginate has a weight-average molecular weight of 4 million or more.

8. The biocompatible material according to claim 1, wherein the alginate is in the form of a particle, and the average particle size of the particles of the alginate is 50 µm or more and less than 300 µm.

9. The biocompatible material according to claim 8, wherein the average particle size of the alginate is 110 µm or more and less than 200 µm.

10. The biocompatible material according to claim 1, wherein the aluminum compound is aluminum lactate.

11. The biocompatible material according to claim 1, wherein a content of the aluminum compound is 0.1% by mass to 5.0% by mass with respect to a total mass of the biocompatible material.

12. The biocompatible material according to claim 1, wherein a content of the aluminum compound is 1.0% by mass to 4.5% by mass with respect to a total mass of the biocompatible material.

13. The biocompatible material according to claim 1, wherein an aqueous solution of the carboxyvinyl polymer having a concentration of 0.5% by mass has a viscosity of 20,000 cP or less at pH 7.5.

14. The biocompatible material according to claim 1, wherein a content of the alginate is 5.0% by mass to 35.0% by mass with respect to a total mass of the biocompatible material.

15. The biocompatible material according to claim 1, wherein a content of the alginate is 10.0% by mass to 30.0% by mass with respect to a total mass of the biocompatible material.

16. The biocompatible material according to claim 1, wherein a value of a ratio of a content of the alginate to a content of the carboxyvinyl polymer is 0.5 to 5.5.

17. The biocompatible material according to claim 1, wherein a value of a ratio of a content of the alginate to a content of the carboxyvinyl polymer is 1.0 to 5.5.

18. The biocompatible material according to claim 1, wherein the oil-based base material contains a gelated hydrocarbon.

19. The biocompatible material according to claim 1, wherein a value of a ratio of a content of the alginate to a content of the oil-based base material is 0.20 to 0.50.

20. The biocompatible material according to claim 1, wherein the biocompatible material is for living body protection.

21. The biocompatible material according to claim 1, wherein the biocompatible material is a mucous membrane protective agent.

22. The biocompatible material according to claim 21, wherein the biocompatible material is an oral cavity mucous membrane protective agent.

* * * * *